United States Patent [19]

Makula et al.

[11] Patent Number: 4,874,708
[45] Date of Patent: Oct. 17, 1989

[54] PROCESS FOR THE PREPARATION OF INTRA-VENOUSLY ADMINISTERED GAMMA-GLOBULINS AND THE GAMMA-GLOBULINS OBTAINED

[76] Inventors: Marie-France Makula, La Cerisaie, 18D rue de Tourvielle, 69 005 Lyon; Jacques Liautaud, Le Petit Paris, 69 760 Limonest, both of France

[21] Appl. No.: 12,662
[22] PCT Filed: May 30, 1986
[86] PCT No.: PCT/FR86/00184
 § 371 Date: Jan. 23, 1987
 § 102(e) Date: Jan. 23, 1987
[87] PCT Pub. No.: WO86/06963
 PCT Pub. Date: Dec. 4, 1986

[30] Foreign Application Priority Data
May 30, 1985 [FR] France ................................ 85 08094

[51] Int. Cl.$^4$ ................................................ C07K 3/12
[52] U.S. Cl. ........................................ 435/272; 435/68; 530/387; 530/388; 530/412
[58] Field of Search ............................ 435/272, 68–71; 530/380, 387, 389, 412

[56] References Cited

U.S. PATENT DOCUMENTS 4,093,606  6/1978  Coval ................................... 424/87
4,312,949  1/1982  Ahrens ................................. 435/272

OTHER PUBLICATIONS

Walsh—13th Int. Congress of IABS—Develop. Biol. Standard, vol. 27 (1974), pp. 31–36.
Walsh—Chem. Abst., vol. 81 (1974), pp. 149961u.
Favreau et al—Experientia, vol. 39 (1983), pp. 483–487.

Primary Examiner—Sam Rosen
Attorney, Agent, or Firm—Larson and Taylor

[57] ABSTRACT

A solution of gamma-globulins, coming for example from Cohn's fractionation, is submitted to a step of fractionation with polyethylene-glycol, a step of moderated enzymatic treatment with pepsin, plasmin or papain, and a step of PEG elimination.

11 Claims, No Drawings

PROCESS FOR THE PREPARATION OF INTRA-VENOUSLY ADMINISTERED GAMMA-GLOBULINS AND THE GAMMA-GLOBULINS OBTAINED

This is why there have already been developed different preparation processes seeking to suppress, or at least to limit this drawback.

A first process seeks to eliminate the aggregates and consists of carrying out a pepsin digestion of the gamma-globulin preparation in such a way as to provoke a rupture of the heavy chains near to the junction of the Fab and Fc fractions. See, for example, the patent FR-A-No. 2,433,342.

Another process, which had been perfected by the applicant, consists of treating a preparation of gamma-globulins with plasmin, in such a way as to provoke a moderated digestion conserving a large proportion (from 30 to 50%) of the gamma-globulins intact and giving the Fab and Fc fragments. This preparation is active and very well tolerated.

A drawback of these different processes which seek to reduce the anti-complement power present is that they require a more or less extensive digestion of the gamma-globulins. Also, the processes seek a compromise between the innocuousness and the activity of the preparation.

One may equally cite diverse preparation processes forming chemically modified gamma-globulins: alkylation, reduction, sulfonation.

Patent FR-A-No. 2,301,266 recommends not carrying out enzymatic treatment, notably with pepsin, of the gamma-globulins and to carry out, instead, a polyethylene-glycol fractionation.

Thus, there has been perfected a process for the preparation of gamma-globulins by polyethylene-glycol (PEG) fractionation which presents the advantage of preventing the formation of aggregates or of eliminating them, while conserving the globulins intact.

In addition, although at diverse degrees, the different preparations described above may present shock factors by activating of the kallikreinbradykinin system. These shock factors appear linked to a residual content of prekallikrein activator.

Another technique, which allows the obtaining of gamma-globulins of good quality, consists of carrying out a treatment at an acid pH, in the presence of small quantities of pepsin. See, for example, J. J. Walsh: Purification of normal immmunoglobin for intravenous use. DEVELOP. BIOL. STAND. 1974, 27, 31-6. However, there still remain aggregates and dimers at a relatively high level.

One has equally proposed, in patent application EP-A-O No. 120 835, to avoid using treatments with pepsin or plasmin, that these enzymes be rendered insoluable or not, to propose a digestion with pancreatic enzymes accompanied by a treatment with polyethylene-glycol at a relatively high concentration. However, this gamma-globulin is not balanced in sub-classes.

The present invention proposes to furnish preparations of gamma-globulins administratable intravenously, at the same time deprived of aggregates and of dimers, deprived of anti-complement power and deprived of kallikrein and of prekallikrein activator and with a profile of sub-classes comparable to that of normal Human Serum.

Another objective of the invention is to furnish such a process which, applied to preparations of gamma-globulins prepared by fractionation with low levels of PEG or analog substances, ameliorates these preparations in diminishing notably the anti-complement power, the content of kallikrein and of prekallikrein activator, as well as the residual PEG.

The invention has for object a process for the preparation of gamma-globulins administratable intravenously, characterized in that it includes a fractionation step with polyethylene-glycol (PEG) or similar substances and a moderated enzymatic treatment step, in which the pH is dependent on the nature of the enzyme used, this being added preferably in the form of traces, the treatment being conducted so as to avoid an appreciable proteolysis.

The enzyme used is chosen from the group formed by the pepsins, fibrinolysins (plasmin), and papains.

The starting material is a fraction of serum origin rich in gamma-globulins such as Cohn's Technique 6.9 fraction II, known to give hepatitis-free products, or a fraction of placental origin such as the fraction of Cohn's technique 6.9 as modified by Taylor. This fraction has a purity in IgG superior or equal to 90%. It may contain variable quantities of albumin which may reach up to 10%.

1st Example

1 - Precipitation with PEG

The starting raw material consists in the dissolving of the precipitate and a clarification of this solution, solution which contains in general from 1 to 4% of proteins. One proceeds to a step of precipitation by addition of polyethylene-glycol (PEG), of molecular weight 4000, in such a way as to obtain a concentration of PEG of 5%. The pH is adjusted to 5.8 by N acetic acid or 0.1 N HCl and the temperature maintained between 0° amd 4° C. The ionic strength is very low, of the order of 0.02.

One thus obtains a precipitate which contains the aggregates that one then separates from the solution by simple decantation, by filtration, or by centrifugation. The precipitate is eliminated.

On the supernatant which results, one then carries out a new precipitation, without new addition of PEG, at the same temperature, but increasing the ionic strength to 0.05 by addition of NaCl of 0.05% to 0.2% and preferably 0.1% and bringing the pH from 7 to 8.5 and preferably 8.0.

The gamma-globulins then precipitate and one separates the precipitate thus formed from the liquid phase by decantation or centrifugation.

This precipitate contains the gamma-globulins deprived of high molecular weight aggregates, but may still contain a level neighboring 10% of dimerized proteins. The electrophoretic purity of this product is superior or equal to 90%. It may contain albumin. The anti-complement activity is very weak. The level of kallikrein and of the activator of prekallikrein is reduced, but these may still exist at variable levels, according to the level in the starting material used.

2 - Moderated enzymatic treatment

The gamma-globulin precipitate is put into pyrogen-free water in such a way as to obtain a concentration of 20 g/l of gamma-globulins. One adds 50 g/l of sucrose and 0.002 g/l of pepsin, the temperature being brought to and maintained at 37° C., the pH being adjusted to 4.1 and one incubates for 24 hours.

One prefers to use the pepsin in solution, in an undissolved form on classical supports. The incubation is carried out over 10 to 96 hours, at this temperature, according to the quantity of enzymes used. After treatment, the pH is neutralized.

3 - Subsequent treatment

One carries out an ultrafiltration, in such a way as to bring the concentration of the solution of the gamma-globulins to 70 g/l.

This ultrafiltration step is followed by a diafiltration destined to eliminate the PEG. This diafiltration is carried out by a solution of NaCl 4.5 g/l. The volume of the diafiltration solution to be used is a function of the level of PEG to eliminate. Generally, a volume corresponding to 8 times that of the IgG solution permits the elimination of over 90% of the PEG initially contained in the solution and thus to pass from a level of 1.5 g/l to 0.10 g/l.

One then carries out the adjustment of the solution obtained to 50 g/l protein, 50 g/l sucrose, 4.5 g/l sodium chloride, at pH 7.0.

One then distributes the substance into flasks of 0.5–2.5 or 5 g of gamma-globulins, then one carries out a lyophilization.

2nd Example

The starting raw material consists of the dissolving of the precipitate and a clarification of this solution which contains 1 to 12% proteins and, moreover, preferentially 6 to 10% proteins.

Moderated enzymatic treatment

One proceeds to a weak treatment with human plasmin. The concentration of human plasmin is from 0.5 to 4 caseinolytic units per gram of proteins.

The incubation temperature is from 0° to 37° C., preferably 4°. The pH is from 6.0 to 8.0, preferably 7.4.

The incubation time depends on the temperature and the quantity of enzyme used: from 2 days to 10 days.

2 - Precipitation of PEG

One proceeds to a step of precipitation of the protein solution which contains in general 1 to 4% of proteins by addition of polyethylene glycol (PEG), of molecular weight 4000, in such a way as to obtain a PEG concentration of 5%. The pH is adjusted to 5.8 by N acetic acid or 0.1 N HCl and the temperature maintained between 0° and 4° C. The ionic force is very low, of the order of 0.02.

One obtains thus a precipitate which contains aggregates that one then separates from the solution by simple decantation, by filtration, or by centrifugation. The precipitate is eliminated.

On the supernatant which results, one then carries out a new precipitation, without new addition of PEG, at the same temperature, but inceasing the ionic strength to 0.05 by addition of NaCl of 0.05% to 0.2% and bringing the pH from 7 to 8.5 and preferably 8.0.

The gamma-globulins then precipitate and one separates the precipitate thus formed from the liquid phase by decantation or centrifugation.

3 - Subsequent treatment

One carries out an ultrafiltration in such a way as to bring the concentration of the solution of the gamma-globulins to 70 g/l.

This ultrafiltration step is followed by a diafiltration destined to eliminate the PEG. This diafiltration is carried out by a solution of NaCl 4.5 g/l. The volume of the diafiltration solution to be used is a function of the level of PEG to eliminate. Generally, a volume corresponding to 8 times that of the IgG solution permits the elimination of over 90% of the PEG initially contained in the solution and thus to pass from a level of 1.5 g/l to 0.10 g/l.

One then carries out the adjustment of the solution obtained to 50 g/l protein, 50 g/l sucrose, 4.5 g/l sodium chloride, at pH 7.0.

One then distributes the substance into flasks of 0.5–2.5 or 5 g of gamma-globulins, then one carries out a lyophilization.

The analysis of the gamma-globulins obtained according to the invention shows the following advantages:

Diminution of the anti-complement power in the different techniques of determination used.

The sub-classes are balanced.

Absence of antihypertensive factors demonstrated by tension test on the dog and on the rat.

Diminution of the level of dimerized proteins by more than 50% relative to the initial level and the obtaining of a very high level of monomers (more than 90%).

Level of fragments less than 7 S null or very low.

Levels of kallikrein and of the acivator of prekallikrein null (less than the sensitivity limit of the test).

Level of residual PEG diminished by more than 10 times relative to the original level.

Although the invention be described in relation to particular embodiments, it is well understood that it is in no way limited to them and that one may bring diverse modifications to it without for all that leaving either its scope or its spirit.

We claim:

1. A process for the production of gamma-globulins free of aggregates, dimers and kallikrein and administratable intra-venously, comprising subjecting a fraction rich in gamma-globulins to fractionation with polyethylene-glycol (PEG) and to a step of controlled enzymatic treatment with an enzyme selected from the group consisting of pepsins, plasmins and papains, said enzymatic treatment being conducted at a suitable pH and in a manner that avoids appreciable proteolysis.

2. The process according to claim 1, characterized in that the step of enzymatic treatment is carried out in the presence of traces of pepsin at an acid pH.

3. The process according to claim 1, characterized in that the step of enzymatic treatment is carried out in the presence of human plasmin and at a neutral pH.

4. The process according to claim 1, characterized in that the step of fractionation is carried out in the presence of around 5% PEG at pH 5.8, and low temperature, notably from +2° to +4° C. at a very low ionic strength, of the order of 0.02, followed by a second precipitation at a higher ionic strength of the order of 0.05 and a pH of pH 8.0.

5. The process according to claim 1, characterized in that the step of fractionation is carried out in the presence of albumin.

6. The process according to claim 2, characterized in that the treatment is carried out with pepsin at a rate of the order of 0.002 g per liter of pepsin for a solution of 20 g per liter of gamma-globulin in the presence of sucrose and an acid pH greater than or equal to 4.

7. The process according to claim 2, characterized in that one uses a pepsin in an insolubilized form.

8. The process according to claim 3, characterized in that the treatment is carried out with human plasmin at a rate of 0.5 to 4 CU/g of proteins and at a neutral pH.

9. The process according to claim 6, characterized in that the incubation lasts, according to the level of enzyme, from 10 hours to 10 days.

10. The process according to claim 1, characterized in that one then proceeds to an ultrafiltration to concentrate the proteins, then a diafiltration for the elimination of PEG.

11. Preparation of gamma-globulins administratable intra-venously obtained by the process according to claim 1.

* * * * *